United States Patent [19]

Layng et al.

[11] Patent Number: 5,077,016
[45] Date of Patent: Dec. 31, 1991

[54] APPARATUS FOR PRODUCING GAS-AIR CONCENTRATIONS

[75] Inventors: Richard E. Layng, Canton Township; Linda Deschere, Farmington Hills; Gunther J. Evanina, Southfield; Purnachandra G. Pai, Birmingham, all of Mich.

[73] Assignee: Michigan Consolidated Gas Company, Detroit, Mich.

[21] Appl. No.: 245,685

[22] Filed: Sep. 16, 1988

[51] Int. Cl.$^5$ .............................................. B01L 5/00
[52] U.S. Cl. ..................................... 422/99; 137/896; 137/897; 73/19.01; 366/101; 366/177; 366/182
[58] Field of Search .............. 73/61.1 R, 23.41, 23.42, 73/29.01, 19.01; 137/896, 897, 602, 606; 261/76; 366/101, 76, 177, 182; 422/99

[56] References Cited

U.S. PATENT DOCUMENTS 3,905,222  9/1975  Boillot ................................ 73/19.01

FOREIGN PATENT DOCUMENTS 8503458  8/1985  European Pat. Off. ............ 366/101

Primary Examiner—Robert J. Warden
Assistant Examiner—Laura E. Collins
Attorney, Agent, or Firm—Harness, Dickey & Pierce

[57] ABSTRACT

Accordingly, the present invention is an apparatus for mixing gas and air to obtain a plurality of predetermined gas-air concentrations including means for supplying gas from a constant pressure gas source. A conduit has a first end connected to the supplying means and a second end connected to a means for diffusing air with the gas to obtain a predetermined gas-air concentration.

6 Claims, 2 Drawing Sheets

APPARATUS FOR PRODUCING GAS-AIR CONCENTRATIONS

BACKGROUND OF THE INVENTION

1. Field of the Invention

This present invention relates to fluid mixtures, more particularly to, an apparatus for mixing natural gas and air to obtain various predetermined gas-air concentrations.

2. Description of Related Art

The odor intensity of gas-air mixtures is useful in determining compliance with the gas safety code requirements in many states. These codes typically require that the natural gas should be odorized such that it can be smelled by a person at a predetermined concentration of, for example, one-fifth the lower flammability limit of the gas (i.e., one percent of gas in air).

An example of an apparatus used for producing a gas-air mixture is found in U.S. Pat. No. 4,106,910, issued Aug. 15, 1978, to Saunders. This patented apparatus uses a venturi and pressurized air for mixing gas with air by dilution.

One problem with the above patented apparatus is that it does not operate adequately in low pressure applications. Another problem is that the apparatus requires pressurized air for mixing the gas and air to obtain the gas-air concentration. It is, therefore, believed that a need exists to produce various gas-air concentrations at low pressures without the use of pressurized air.

It is one object of the present invention to provide an apparatus for mixing gas and air at various predetermined concentrations. It is another object of the present invention to provide an apparatus that mixes gas and air at low pressures. It is still another object of the present invention to mix gas and air without the use of pressurized air.

SUMMARY OF THE INVENTION

Accordingly, the present invention is an apparatus for mixing gas and air to obtain a plurality of predetermined gas-air concentrations including means for supplying natural gas from a constant pressure natural gas source. A first conduit has a first end connected to the supplying means and a second end connected to a control valve for controlling the amount of gas exiting the first conduit. A second conduit has a third end connected to the control valve and a fourth end connected to a means for diffusing air with the natural gas to obtain a predetermined gas-air concentration.

One advantage of the present invention is that the apparatus mixes natural gas and air at various predetermined concentrations for use in sniff or odor intensity tests. Another advantage of the present invention is that the mixing process occurs by diffusion, making it possible for low pressure application. A further advantage of the present invention is that the mixing occurs by diffusion, eliminating the need for pressurized air.

Other advantages of the present invention will be readily appreciated as the same becomes better understood by reference to the following detailed description when considered in connection with the accompanying drawings.

DESCRIPTION OF THE PREFERRED EMBODIMENT

Figure 1:
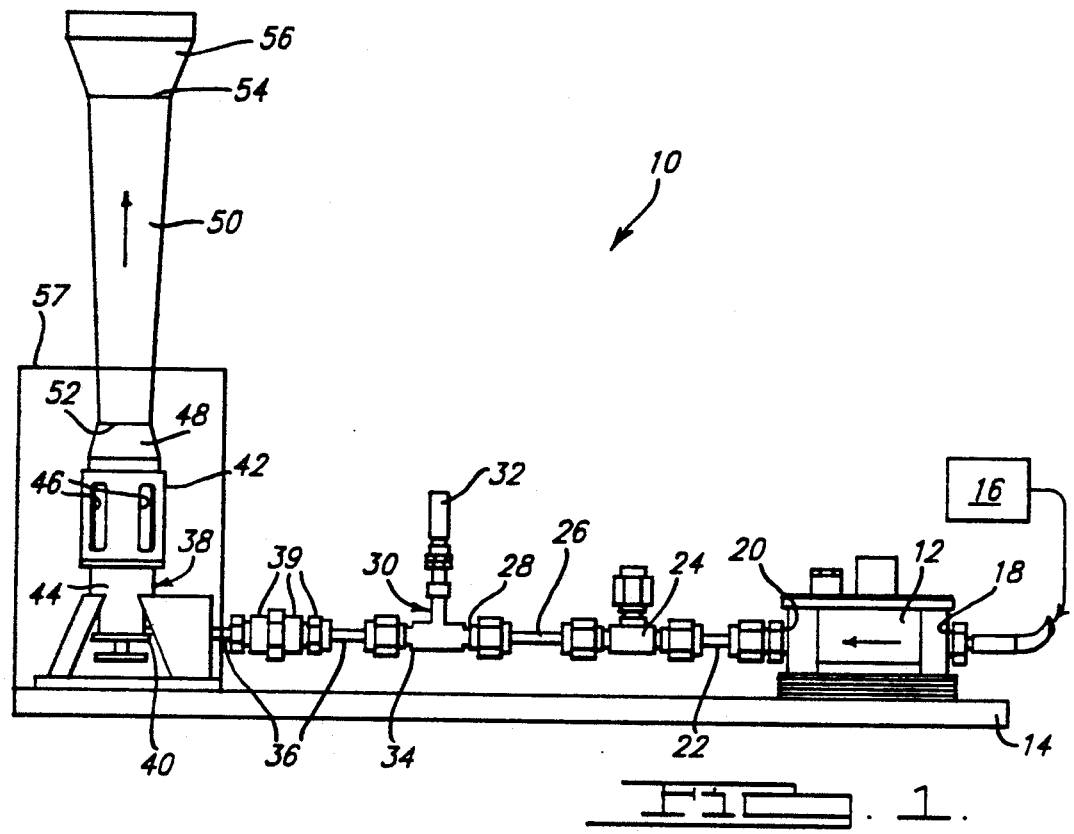
FIG. 1 is an elevational view of an apparatus constructed in accordance with the principles of the present invention.

FIG. 1 depicts an apparatus 10 for mixing a plurality of fluids such as natural gas and air at various predetermined concentrations, e.g. 0.5% gas in air, 1.0% gas in air, etc. These mixtures are typically utilized for sniff tests, commonly known in the art, to determine the odor intensity of the natural gas. The apparatus 10 includes a regulator 12 mounted to a support surface 14 for supplying natural gas from a constant pressure natural gas source 16. The regulator 12 has an inlet 18 and an outlet 20. Pressurized natural gas flows from the outlet 20 through a conduit 22, typically made of stainless steel tubing, to an optional "T" shaped conduit 24 used in non-production development. The natural gas flows through the conduit 24 and a connecting conduit 26 to an inlet 28 of a control valve 30. The control valve 30 is also "T" shaped and has a handle 32 and an outlet 34. The handle 32 is rotated about its axis so that the control valve 30 controls the flow of natural gas through its outlet 34. The handle 32 of the control valve 30 is lockable in position after adjustment by any suitable means. The control valve 30 may be an adjustable conventional needle valve to vary the amount of natural gas through it. The pressurized natural gas flows from the outlet 34 and through a conduit 36 to a diffusion member 38. It will be appreciated by those skilled in the art that the conduits and other components are connected to each other by means such as coupling members or conduit adapters 39. The pressurized natural gas flow through the diffusion member 38 aspirates air which mixes with the gas to provide a desired predetermined concentration of gas in air. In other words, the diffusion member 38 uses natural convection to allow the gas and air to aspirate into one another to produce the desired predetermined gas-air concentration.

The diffusion member 38 is generally cylindrical in shape and extends substantially vertically upward from the support surface 14. The diffusion member 38 has an inlet 40 for receiving the pressurized natural gas from the conduit 36. The diffusion member 38 also includes an adjustment member 42 which is generally a cylindrical sleeve which fits over or about a plurality of apertures (not shown) formed in a base portion 44 of the diffusion member 38. The adjustment member 42 includes a plurality of circumferentially spaced elongated or elliptical apertures 46 formed therein to adjust the amount of air entering through the apertures 46 into the base portion 44 of the diffusion member 38. The adjustment member 42 is rotated about the base portion 44 to open and close the apertures in the base portion 44. Alternatively, the diffusion member 38 may include a plurality of apertures, such as the elliptical apertures 46 formed in the base portion 44 to allow a fixed amount of air to enter the diffusion member 38. The gas and air exit the end 48 of the base portion 44 into a stack member 50. The gas and air are mixed together or diffused one into the other in the stack member 50. The stack member 50 is generally cylindrical in shape and a first end 52 which tapers radially outwardly to a larger diameter second end 54. A frustoconical shaped portion 56 is connected to the second end 54. The gas-air mixtures exit the portion 56 at the desired predetermined concentration which can be verified by means such as gas chromotographical analysis. For odor intensity tests, a person would place their nose at the exit of portion 56 for sniff checks. The apparatus 10 also includes a shroud 57 having a generally cylindrical tubular shape placed about the base portion 44 to minimize the effects of room air currents. The shroud 57 provides consistent results to the odor intensity tests by allowing the diffusion process to occur without the effects of air currents.

Figure 2:
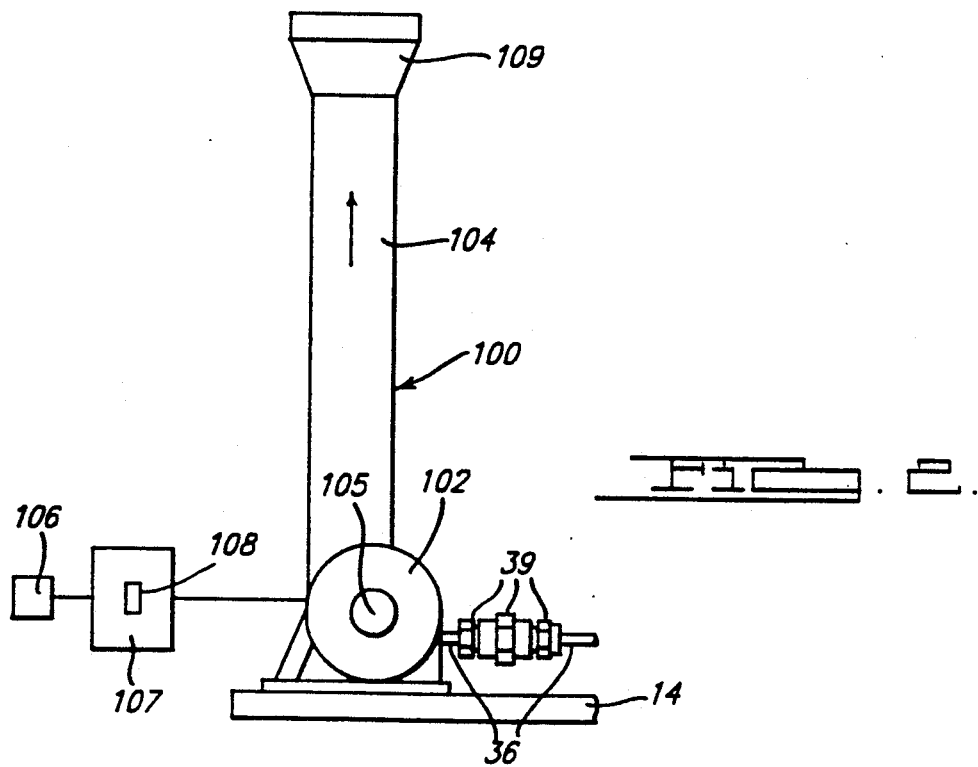
FIG. 2 is an elevational view of an alternate embodiment for the diffusion member of FIG. 1.

FIG. 2 depicts an alternate embodiment of the diffusion member 38 of FIG. 1. The diffusion member 38 is replaced with a fan operated diffusion member 100 having a blower or fan 102 at one end connected to a generally cylindrical stack member 104. Air enters the blower 102 through an inlet 105 in the blower 102. To maintain portability for field use, the blower 102 is driven or powered by batteries 106. A constant voltage circuit 107 is placed between the batteries 106 and blower 102 to provide a constant fan or blower speed over the life of the batteries 106. A typical conventional and known constant voltage circuit may be used. In addition, an optional low battery voltage detection and warning light 108 may be included in the constant voltage circuit 107. The blower 102 is powered by means such as batteries shown in block 106. The stack member 104 has a frustoconical portion 109 at one end of the stack member 104. The gas and air is mixed in the stack member 104. The fan operated diffusion member 100 provides higher quantities of gas-air mixtures than the diffusion member 38 of FIG. 1. The fan operated diffusion member 100 mixes gas and air by aspiration through air entering the inlet 105 of the blower 102.

Figure 3:
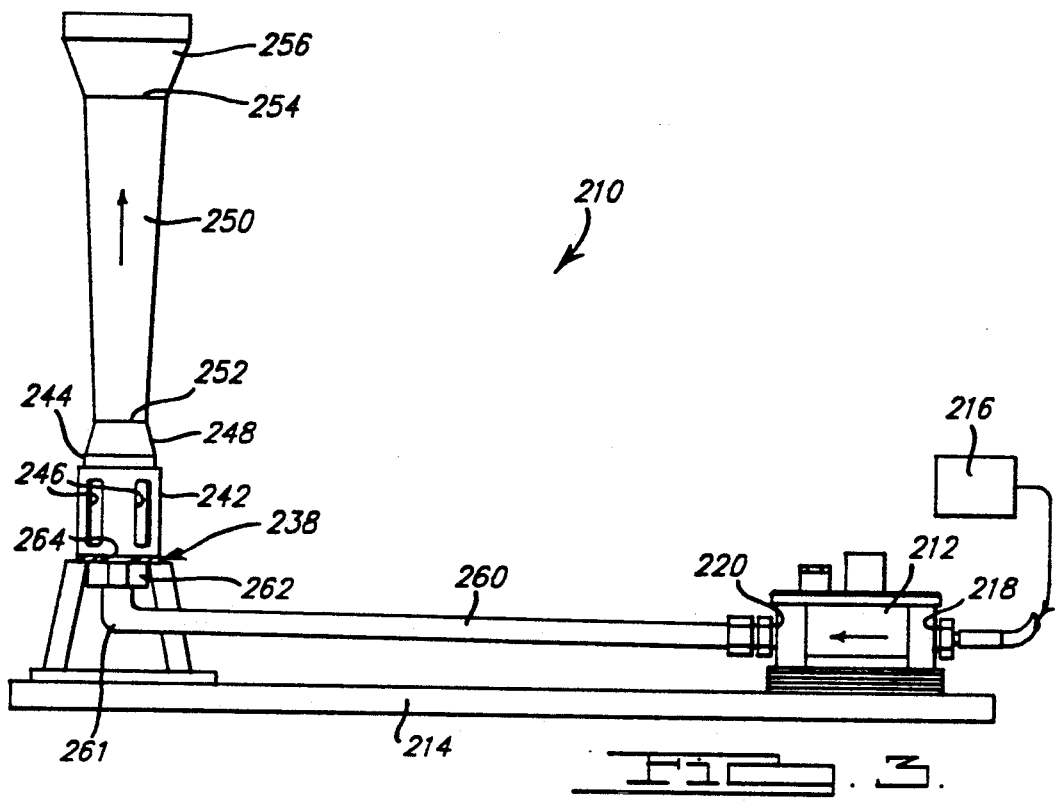
FIG. 3 is an elevational view of an alternate embodiment of the apparatus of FIG. 1 according to the present invention.

Referring to FIG. 3, a commercially preferred embodiment of the apparatus 10 of FIG. 1 is shown. Like parts have like numerals increased by 200. The apparatus 210 eliminates the adjustable needle or control valve and several fittings to reduce the cost. A conduit 260 having a fixed diameter interconnects the outlet 200 of the regulator 212 and the base portion 244 of the diffusion member 238. The base portion 244 includes a connector fitting 262 with press fit gas flow orifice 264 to provide a fixed or predetermined amount of gas flow into the diffusion member 238. The orifice 264 is of a predetermined or fixed diameter and may be formed in a plate at the bottom of the base portion 244 or the inner diameter of the fitting 202. The conduit 260 includes either a pipe elbow (street L) or tube fitting 90° elbow 261. Additionally, the air inlet through apertures 246 may be adjustable or fixed as previously described.

Figure 4:
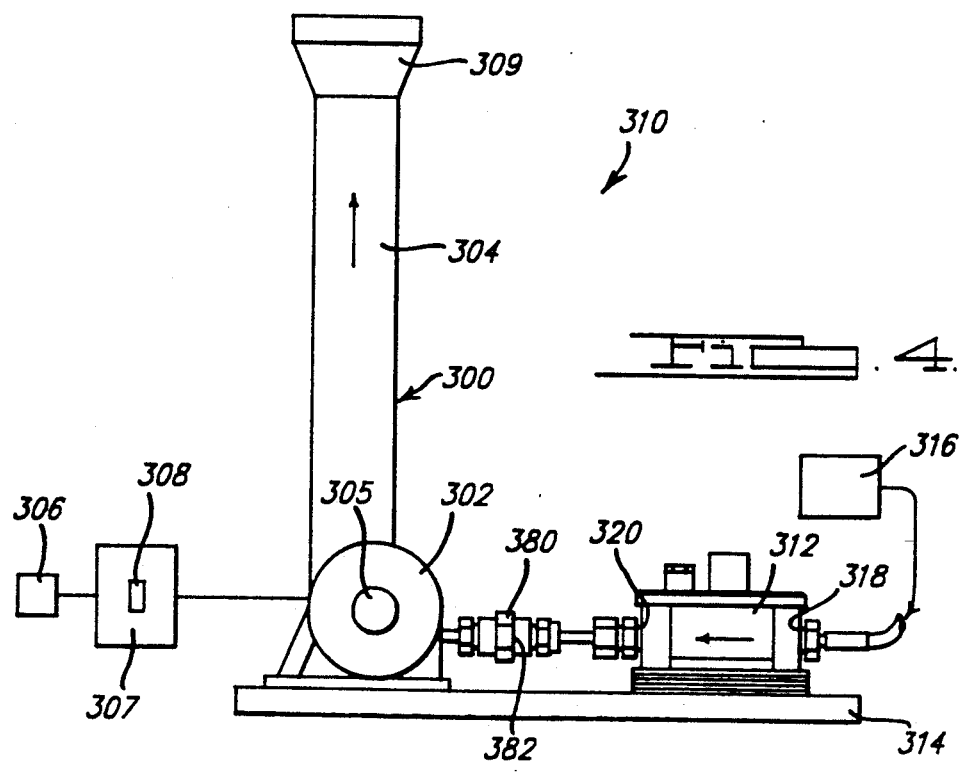
FIG. 4 is an elevational view of an alternate embodiment for the diffusion member of FIG. 3 according to the present invention.

Referring to FIG. 4, a preferred commercial embodiment of the apparatus 210 utilizing the fan operated diffusion member 100 of FIG. 2 is shown. Like parts of FIGS. 2 and 3 have like numerals increased by 100 and 200, respectively. The apparatus 310 includes a fitting 380 with a press fit fixed orifice 382 interconnecting the blower 302 and the regulator 312. The fixed diameter orifice 382 provides a fixed or predetermined amount of gas flow into the fan operated diffusion member 300.

The operation is essentially the same as diffusion member 100.

The present invention has been described in an illustrative manner. It is to be understood that the terminology which has been used is intended to be in the nature of words of description rather than of limitation.

Obviously, many modifications and variations of the present invention are possible in light of the above teachings. Therefore, within the scope of the appended claims, the present invention may be practiced otherwise than as specifically described.

What is claimed is:

1. An apparatus for mixing a plurality of gases to obtain a plurality of predetermined gas concentrations comprising:

means for supplying a first gas from a constant pressure first gas source;

a conduit having first and second ends, said first end being connected to said supplying means; and means connected to said second end of said conduit for diffusing a second gas from a second gas source with the first gas to obtain a predetermined gas concentration, said diffusing means including a base portion connected to said second conduit, and a stack portion connected to said base portion and having an open discharge end opposite said base portion, said stack portion having an internal cross-sectional opening extending therethrough that increases from said base portion to said open discharge end, said diffusing means further including adjustment means for adjusting the amount of said second gas entering said stack portion, said adjustment means being located generally at said base portion and including a number of base portion intake openings extending therethrough in communication with an interior of said stack portion, and a sleeve member generally surrounding said base portion intake openings and being selectively movable thereon, said sleeve having a number of sleeve intake openings extending therethrough, said sleeve being selectively movable between respective positions on said base portion wherein said sleeve intake openings and said base portion openings are at least partially aligned and wherein said sleeve intake openings and base portion openings are at least partially misaligned in order to selectively adjust the amount of said second gas being allowed to enter said stack portion in order to thereby selectively adjust the amount of said second gas being mixed with said first gas therein.

2. An apparatus as set forth in claim 1 wherein said supplying means comprises a regulator.

3. An apparatus as set forth in claim 1 including valve means connected to said conduit between said supply means and said diffusing means for controlling the amount of the first gas exiting said conduit.

4. An apparatus as set forth in claim 3 wherein said valve means comprises a valve having a rotatable handle for controlling the amount of the first gas through said valve.

5. An apparatus as set forth in claim 1 wherein said diffusion means further includes a fixed diameter orifice for providing a predetermined amount of first gas flow into said diffusing means.

6. An apparatus as set forth in claim 1 wherein said stack member is of a generally conical configuration and has a first end of a smaller diameter connected to said base portion and a tapered portion extending axially to said open end of a larger diameter.

* * * * *

UNITED STATES PATENT AND TRADEMARK OFFICE
CERTIFICATE OF CORRECTION

PATENT NO. : 5,077,016

DATED : December 31, 1991

INVENTOR(S) : Richard E. Layng et al.

Page 1 of 2

It is certified that error appears in the above-identified patent and that said Letters Patent is hereby corrected as shown below:

ON THE TITLE PAGE, under "References Cited", "U.S. PATENT DOCUMENTS", the following should be added:

--4,722,217  2/88   Arnett et al.
  4,550,590  11/85  Kesson
  4,534,204  8/85   Bergquist
  4,489,590  12/84  Hadden
  4,485,665  12/84  Norman
  4,384,925  5/83   Stetter et al.
  4,304,120  12/81  Myers et al.
  4,262,522  4/81   Reich
  4,257,439  3/81   Mayeaux
  4,254,797  3/81   Mayeaux
  4,134,289  1/79   Bohl et al.--

Column 3, line 48,
   "200" should be --220--.

UNITED STATES PATENT AND TRADEMARK OFFICE
CERTIFICATE OF CORRECTION

PATENT NO. : 5,077,016

DATED : December 31, 1991

INVENTOR(S) : Richard E. Layng et al.

It is certified that error appears in the above-identified patent and that said Letters Patent is hereby corrected as shown below:

Column 4, line 44, claim, after "and", insert --said--

Signed and Sealed this

Thirty-first Day of August, 1993

Attest:

BRUCE LEHMAN

Attesting Officer    Commissioner of Patents and Trademarks